US00PP10861P

United States Patent [19]

Mak

[11] Patent Number: Plant 10,861

[45] Date of Patent: Apr. 20, 1999

[54] ORIENTAL LILY PLANT NAMED 'LE CHIC'

[75] Inventor: Nicolaas Aloysius Maria Mak, Zand, Netherlands

[73] Assignee: Cebeco Lilies, Inc., Aurora, Oreg.

[21] Appl. No.: 08/903,189

[22] Filed: Jun. 10, 1997

[30] Foreign Application Priority Data

Jun. 26, 1996 [EP] European Pat. Off. ..... 733/96

[51] Int. Cl.[6] ..... A01H 5/00

[52] U.S. Cl. ..... Plt./315

[58] Field of Search ..... Plt./87.4, 315

[56] References Cited

U.S. PATENT DOCUMENTS

P.P. 5,189 2/1984 Kirsch ..... Plt./87.4

*Primary Examiner*—Howard J. Locker
*Assistant Examiner*—Kent L. Bell
*Attorney, Agent, or Firm*—Klarquist Sparkman Campbell Leigh & Whinston, LLP

[57] ABSTRACT

A new and distinct Oriental Lily Hybrid having numerous, medium large, upright, pink flowers and forming a striking inflorescence with tall, strong stems for cut flower production.

2 Drawing Sheets

BACKGROUND OF THE INVENTION

The present invention relates to a new and distinct cultivar of Lilium hybrid referred to commercially as an upright Oriental lily hybrid and named 'Le Chic'.

This invention was found in a greenhouse production bed of 'Le Reve' (U.S. Plant Pat. No. 5,189) and is thought to be a somaclonal mutation. It is an improvement with its larger flowers, increased stem strength, and taller stems; a definite advantage in cut flower production. It also shows no leaf scorch, another improvement.

This invention has not been observed under all possible environmental conditions. The phenotype may vary significantly with variations in environment such as temperature, light intensity and day length, without, however, any variation in genotype.

The following traits have been repeatedly observed and are determined to be the basic characteristics of this invention which in combination distinguish this lily as a new and distinct cultivar: (1) floriferous habit; (2) medium large, upright, pink flowers; (3) vigorous growth habit; (4) large buds; (5) strong stems; (6) virus tolerance; (7) desirable forcing time. Bulbs of this plant may be precooled and forced out of season for very uniform cut flower production.

The primary distinguishing features of the invention are its large numerous light pink flowers. Compared to Lilium 'Le Reve' (U.S. Plant Pat. No. 5,189), this invention has larger flowers, deeper pink color, taller, stronger stems, larger, wider leaves, and blooms two weeks later. Otherwise, they are very similar.

Asexual reproduction of this new variety has been accomplished at Cebeco Lilies, Inc., Aurora, Oreg. by scaling and tissue culture. The resulting plants have shown that the above-mentioned unique features are stable and reproduce true to type in each successive propagation.

Figure 1:
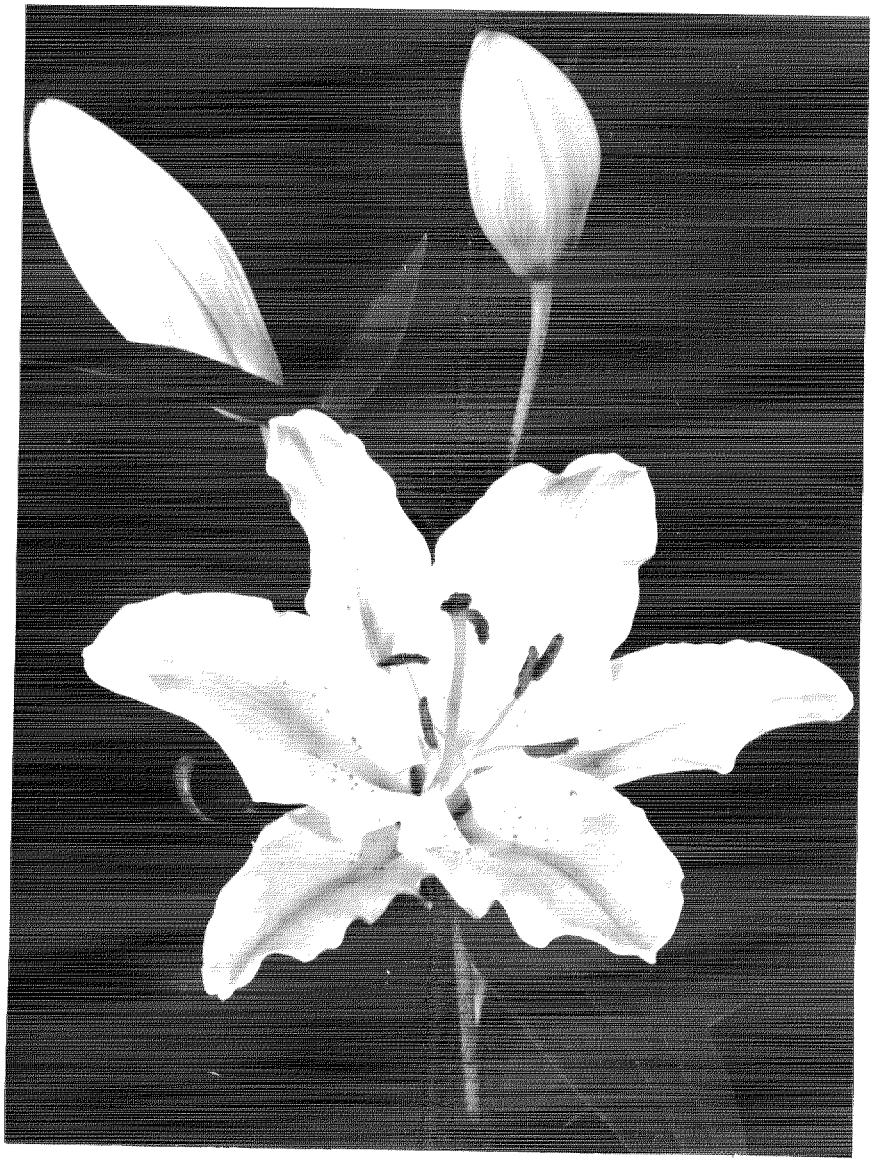
FIG. 1 is a close-up photograph which illustrates a single flower and buds in various stages of development of the new plant.
Figure 2:
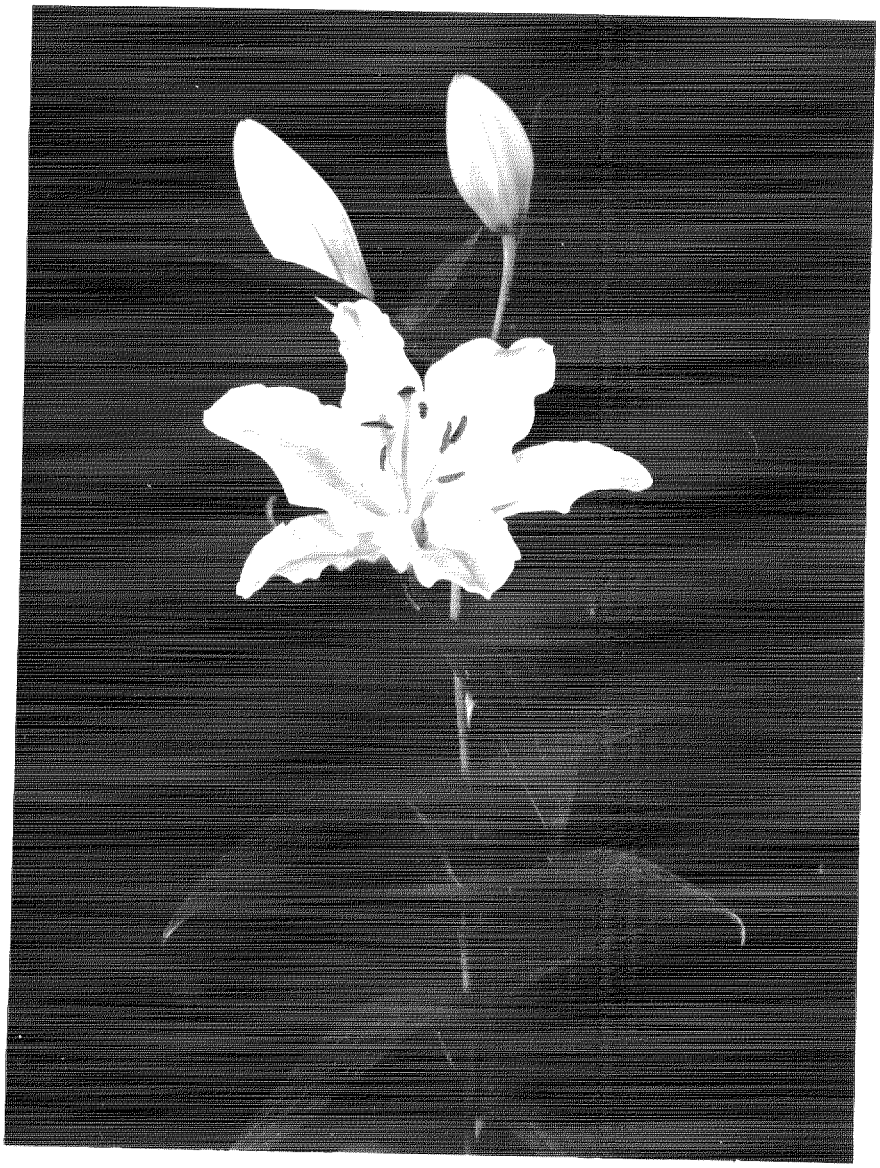
FIG. 2 is a photograph showing a flowering stem of the 'Le Chic' lily.

The photographs of the drawing were taken in December 1996 in a studio and illustrates the typical flower and foliage form, with color as true as reasonably possible in this type of color photograph.

DETAILED DESCRIPTION

The following is a detailed description of the invention based on plants produced under commercial practices in the Cebeco Lillies, Inc. greenhouses in Aurora, Oreg. in December 1996. Color references are made to The Royal Horticultural Society Colour Chart, except where the context indicates a term having its ordinary dictionary meaning.

THE PLANT

Origin: Mutation.

Parentage: 'Le Reve' (U.S. Plant Pat. No. 5,189).

Commercial classification: Upright Oriental lily cultivar.

classification: Division IV, Oriental Hybrid, Subdivision b. Bowl-shaped flowers, according to the Horticultural Classification of Lilies by The Royal Horticultural Society of London.

Form: Single erect stem bearing terminal cluster of large flowers.

Height: From about 99 cm. from the top of the soil to the top of the inflorescence.

Growth habit: Vigorous, upright and rigid.

Foliage:

- *Arrangement.*—Spiral.
- *Quantity.*—Average.
- *Leaf size.*—Variable to about 17 cm. long and about 4.2 cm. wide.
- *Leaf shape.*—Lanceolate.
- *Leaf margin.*—Entire.
- *Texture.*—Leathery.
- *Aspect.*—Glossy.
- *Color.*—Very deep green on both sides (147A topside, 147B bottomside).

Bulbs:

- *Size.*—Variable, ranging to about 14 to 20 cm. in circumference as used commercially.
- *Color.*—White with yellow and pink overtones (more prominent with age).

THE BUD

Size: Large and wide, to about 11 cm. long and 4.2 cm. wide just prior to opening.

Shape: Ovoid with the apex commonly having three obtuse tips.

Rate of opening: The mature bud opens slowly in response to light.

Color: Pink, midribs are light green. Red- Purple Group 63D.

THE FLOWER

Blooming habit: Annually, once and profusely, mid season.

Days to bloom: Flowers approximately 109–119 days after spring greenhouse planting under typical commercial flower forcing conditions of 17 degrees Celsius night time temperatures.

Flower size: Medium large.

*Diameter.*—To about 16.5 cm.

Borne: Raceme of about six flowers from bulbs 16 cm. in circumference.

Shape: When the flower first opens it is bowl shaped. Later the shape flattens out slightly and the tepals reflex at the tips.

Tepalage:

*Number.*—Six.

*Texture.*—Waxy.

*Aspect.*—Satiny, glossy.

*Margins.*—Undulate, especially outer tepals.

*Size.*—Lenght: About 11 cm. Width: Inner tepals—about 5 cm. Outer tepals —about 4 cm. Depth of Imbrication: About 2 cm.

*Nectary.*—Light green (Yellow-Green Group 144A) smooth, oozing, 3 cm. long, surrounded with yellow gold (Yellow Group 2A–4A).

*Projections:*—Papillae present of tepals and are about 20 in number.

*Spots.*—Oblong, maroon, on bottom half of tepals, raised, Greyed-Purple Group 187C.

*Blush.*—Yellow right around the nectary, Yellow Group 2A.

*Color.*—Pink, darkest at the midvein and lightening toward the margins and base alongside the nectary where it is white. Topside: Red-Purple Group 68C—D/ Bottomside: Red-Purple Group 65A, around the midrib slightly lighter and tepal bases slightly darker.

*Fragrance.*—Sweet.

*Lasting quality:*—Excellent. Each flower lasts about five to twelve days depending upon environmental variables.

Pedicel:

*Color.*—Yellow green with maroon spots on the top.

*Orientation.*—Ascending upwardly off the stem at about a 45–55 degree angle.

THE REPRODUCTIVE ORGANS

Stamens:

*Number.*—Six, typical of the genus Lilium.

*Filaments.*—To about 8 cm. Color: Yellow-Green Group 150 C.

*Anthers before dehiscence.*—Length: About 28 mm long. Color: Greyed-Purple Group 184A.

*Pollen.*—Color: Deep rust, Greyed-Orange Group 171A.

Pistil:

*Number.*—One.

*Style.*—Length: About 9 cm. Color: Green, Green Group 144A.

*Stigma.*—Color: Maroon. Greyed-Purple Group 187A.

THE FRUIT

Fertility: The fruit is fertile. Shape: Ovoid. Color at maturity: Soft Brown.

I claim:

1. A new and distinct cultivar of hybrid Oriental lily plant substantially as herein shown and described.

* * * * *